US005527531A

United States Patent [19]

Linhart

[11] Patent Number: 5,527,531

[45] Date of Patent: Jun. 18, 1996

[54] SYNTHETIC BAIT FOR DELIVERY OF CHEMICALS AND BIOLOGICS

[75] Inventor: Samuel B. Linhart, Grayson, Ga.

[73] Assignee: The United States of America as represented by the Department of Agriculture, Washington, D.C.

[21] Appl. No.: 691,873

[22] Filed: Apr. 26, 1991

[51] Int. Cl.[6] .......... A01N 25/08

[52] U.S. Cl. .......... 424/410; 424/84; 424/405; 514/772.3

[58] Field of Search .......... 424/84, 89, 82, 424/451, 452, 408, 410, 442, 486, 438; 514/772.3

[56] References Cited

U.S. PATENT DOCUMENTS

| | | | |
|---|---|---|---|
| 1,419,618 | 6/1922 | Deming | 424/451 |
| 4,496,535 | 1/1985 | Gould et al. | 424/19 |
| 4,642,230 | 2/1987 | Whitehead et al. | 424/438 |
| 5,013,306 | 5/1991 | Solomon et al. | 604/265 |

*Primary Examiner*—Thurman K. Page
*Assistant Examiner*—Neil Levy
*Attorney, Agent, or Firm*—Glenna Hendricks; Stephen Gates; Howard Silverstein

[57] ABSTRACT

This invention is a delivery system to deliver biologics such as vaccines or chemicals such as chemosterilants, repellents, or toxicants to free-roaming or wild animals such as raccoons, dogs, or foxes, without capture or physical restraint. The biologic or chemical is placed in a water-proof ampule or capsule which is imbedded in a synthetic bait comprising attractants and other additives on a polymeric support. The product will stimulate the target species to chew sufficiently that the active agent will be expelled in the oralpharyngeal cavity, particularly against the buccal mucosa. The specific adaptations of the invention depend on the eating habits of the animal species targeted.

17 Claims, No Drawings

SYNTHETIC BAIT FOR DELIVERY OF CHEMICALS AND BIOLOGICS

SUMMARY OF THE INVENTION

This invention is a delivery system to deliver biologics such as vaccines or chemicals such as chemosterilants, repellents, or toxicants to free-roaming or wild animals such as raccoons, dogs, or foxes, without capture or physical restraint. The biologic or chemical is placed in a water-proof ampule or capsule which is imbedded in a synthetic bait comprising attractants and other additives on a polymeric support. The product will stimulate the target species to chew sufficiently that the active agent will be expelled in the oralpharyngeal cavity, particularly against the buccal mucosa. The specific adaptations of the invention depend on the eating habits of the animal species targeted.

BACKGROUND OF THE INVENTION

The administration of active agents for control of populations, treatment of disease, and immunization to animals in the wild presents several problems. First, the active agent must be "packaged" in such a manner that the animal toward whom the active agent is targeted will accept the bait with the agent. The active agent must be protected from disintegration or release into the environment before it reaches the desired targeted animal. Furthermore, the "packaging" must deliver the active agent to the appropriate site in the targeted animal so that maximum effect from the active agent will result. Of particular concern is the immunization of animals against diseases that can be transmitted to man or domesticated animals.

Rabies in dogs and in wildlife is an example of a problem that has been addressed by use of baits containing active agents, in this case, the vaccine. The disease is a persistent and widespread problem in North America as well as in many lesser developed countries of the world. In the United States 88% of all rabies cases reported in 1988 occurred in wild animals. Specific economic loss estimates are lacking. However, about 25,000 post-exposure human rabies treatments are given annually at a cost of about 12 to 13 million dollars. Additional economic factors are cost of vaccine production, laboratory diagnosis and fees, compensatory insurance claims, vaccination of pets and livestock, livestock losses, wildlife and fur resource losses, salaries and operating costs associated with handling rabies outbreaks, posting of infected areas, and control of wildlife vectors. Historically, the federal Animal Damage Control Program has participated in the local reduction of wildlife vector populations as authorized under the Animal Damage Control Act of 1931 and, more recently, under the 1988 USDA Appropriations Act. Both acts authorize the conduct of research on rabies and other zootic diseases as worthy of the attention of the federal government.

In order to effectively immunize a species of against rabies five primary factors must be available: (1) an effective vaccine, (2) baits readily accepted by target species, (3) baiting methods that reach a high proportion of the susceptible population, (4) methods and materials that can be used safely, and (5) acceptable costs for development and use.

Recent developments in oral rabies vaccine technology and delivery systems research in Europe, Canada, and, most recently, in the United States indicate an increased potential for controlling the disease in wildlife using new vaccines. The vaccination approach has biological advantages over population reduction and is far more acceptable to the public, particularly in urban areas of the United States. In addition to use for dogs, an oral vaccine may be useful in controlling rabies in, for example, arctic foxes of Alaska, mongooses of the Caribbean Islands, skunks of the Midwest and California, red foxes of the Northeast, and raccoons of the Mid-Atlantic and Southeast.

The concept of immunizing wildlife using an oral rabies vaccine delivered by bait was first tested with captive red foxes in the early 1960's. Subsequent laboratory studies in Europe and the United States showed further potential for orally immunizing the species. An outbreak of rabies in red foxes in norther Europe that spread through various countries during the 1950–1970's stimulated parallel vaccination studies in Switzerland and West Germany. Canada, Switzerland, West Germany and, more recently, France undertook field studies to determine the potential for baiting fox populations by distributing baits containing physiological markers that indicated which individual animals took baits. Collection of foxes following baiting established that high percentages of target populations had consumed baits. The oral immunization concept found favor in Europe because previously used conventional population reduction techniques such as den destruction and hunting did not appear efficacious for stopping fox rabies. European field studies using baits with markers were followed by widespread application of baits containing rabies vaccine. These efforts have reportedly eliminated fox rabies in most of Switzerland and parts of West Germany. France and Belgium have also initiated field evaluations.

Previous baits used have been described in the patent literature. U.S. Pat. No. 4,014,991 assigned to the U.S. Government describes a plastic elongated polyethylene tube holding attenuated vaccine. The vaccine containing bait of that invention is an ampule surrounded by a meat bait. When the bait is bitten, the vaccine is transferred to the buccal mucosa.

U.S. Pat. No. 4,650,673 of Johnston discloses a sponge that is saturated with liquid vaccine so that significant volumes of the vaccine are expelled upon bite penetration. The sponge vector is coated with a wax containing an attractant such as beef fat. The sponge is filled with vaccine by injection into the sponge. The sponge does not surround the vaccine, but is impregnated with it. The covering is a water-proof wax with attractant. The preferred shape of the baits is cubical.

U.S. Pat. No. 4,752,474 describes and claims an oral vaccine. The primary emphasis of the disclosure is on the vaccine itself. It is simply stated that the vaccine was administered in baits. The particular baits used are not described.

U.S. Pat. No. 4,861,586 describes a prefabricated animal bait wherein the active agent is enveloped by a carrier comprising a fat material and at least one additive to stabilize the shape retention of the bait wherein the lure (attractant), fat, and additive are made into a thick paste. No teaching regarding use of an ampule is disclosed.

DETAILED DESCRIPTION OF THE INVENTION

It is the purpose of this invention to provide a method for delivering active agents to targeted species using baiting methods that reach a high proportion of the susceptible population utilizing materials that can be used safely and at acceptable cost.

The delivery system of the instant invention comprises an edible ampule or capsule holding an active agent enclosed in a synthetic support that is treated and/or coated with attractants. The particular attractant used and the size, texture, hardness, flavor, or odor of the bait is adapted to the species targeted and will vary depending upon behavioral characteristics of the targeted species and the environment into which the baits are to be disseminated. A preferred sleeve is a polymeric sponge with attractants and other additives absorbed in and adsorbed on the sleeve to provide appropriate chewing consistency and protection of the contents of the ampule from the environment. For example, a bait for targeting wild carnivores and dogs used an open cell polyurethane foam sleeve (about 1.5× 5.5 cm with 0.6 cm cavity). The cavity contained a paraffin wax ampule into which the vaccine had been sealed.

The use of the ampule has several advantages. It protects the active ingredient from exposure to the materials used as a bait or present in the environment, thus avoiding contamination and disintegration of the active agent. In this respect the invention instantly taught and claims differs markedly from the invention of Johnston disclosed in U.S. Pat. No. 4,650,673, which involves use of a sponge as a carrier wherein the sponge itself is impregnated with the vaccine.

The use of the sleeve as taught herein as a surrounding for the ampule presents several advantages. First, the sleeve protects the ampule from destruction before ingestion. The sleeve can be made in several sizes and may be treated with attractants particularly effective toward the species targeted. The sleeve should also protect from adverse weather conditions such as prolonged periods of moisture or extremes of temperature. If the active ingredient is an oral vaccine, as exemplified, it is desireable that the bait be readily consumed by the target species within a short time period after distribution. The present invention provides advantages over the baits of U.S. Pat. No. 4,014,991 since the synthetic construction of the novel synthetic baits disclosed herein are less perishable and provide greater protection from environmental conditions that might cause deterioration of the vaccine The baits of the present invention are particularly adapted to cause the target animal to chew vigorously so that the ampule is broken and the vaccine is forced into contact with mucosa of the oralpharyngeal cavity.

The baits of the invention can be made cheaply and easily in large numbers. Such baits can be distributed aerially if desired and are consumed by a high percentage of the target population. For immunization of dogs, baits can be hand-distributed to unowned or free-roaming street dogs without need to capture the animals. They may be cheaply and easily provided to pounds or kennels and may be distributed door to door to dog owners.

Another example of a species particularly susceptible to immunization using the methods of the invention is the raccoon, the major wildlife vector of rabies in the eastern United States.

The contents of the edible ampule or capsule may be in any form, including liquid, powdered, or a gel. For flavoring the baits, various blended essential oils are available from the food flavoring industry and from companies that sell supplies to trappers who use them to make lures and baits for trapping. In testing the instant invention various oils were added to tallow and beeswax of the baits to enhance bait consumption. Baits for raccoons were made containing flavors of various fruits commonly eaten by raccoons (grape, persimmon, and cherry). Other baits contained seafood byproducts such as clam, shellfish, and shrimp oils. Sweet corn oil, anise oil, and a liquid "smoke" flavor were also used. While the oils were usually added to melted tallow and beeswax matrix at about 1% by weight, the amount of flavoring added can vary. Seven different matrixes were tested on the raccoons.

EXAMPLE 1

An open cell polyurethane foam sleeve of 1.5 by 5.5 cm with a 0.6 cm wide capacity (Goody Products, Inc, New York, N.Y. 10121, used for manufacturing women's hair curlers.) was inverted onto wooden dowels fastened to a wooden or plastic plate. The plate with the sleeves was then inverted and the sleeves were dipped into a batter mixture of flour, yellow corn meal, whole milk, and whole egg. The sleeves so coated were then dipped into heated (375°) corn oil and deep fried for approximately 20–30 seconds. The resulting treated sleeves would accommodate a 2.0 ml capacity paraffin wax ampule into which the vaccine had been sealed. The particular vaccine used would depended on the animals.

EXAMPLE 2

Sleeves were loaded with ampules containing a raccoon poxvirus rabies glycoprotein recombinant preparation (RCN-KB3-JE13) at $2\times10^8$ PFU/2 ml of recombinant in phosphate buffered saline (PBS) containing 20% fetal bovine serum. When the baits were administered to caged animals, nine of ten animals developed high levels of rabies antibodies. Thus, it appeared that the baits described were highly effective for immunizing raccoons.

The same baits were field-tested during 1989 in Georgia and Maryland and were determined to be well accepted by wild raccoons in both geographic areas. Raccoons visited a high percent of bait stations (32.3% to 44.3%) and took 79% to 89.9% of the bait packets they visited within 4–5 days. Less than 1.0% of all baits taken were found partially eaten and no rejection of water-filled paraffin ampules contained in baits was observed.

EXAMPLE 3

Foam sleeves of polyurethane from Goody Products, Inc. (See Example 1) were briefly dipped into a matrix of rendered beef tallow (90%) obtained at the local rendering plant, and yellow beeswax (10%) obtained from a trappers supply house and allowed to cool at room temperature. After cooling, the sleeves were dipped in glycerol containing 1% shellfish oil and allowed to drain, after which the they were surface-coated with fish meal.

EXAMPLE 4

In March, 1990, 40 baits of Example 1 were offered to laboratory beagles in a CDC confinement facility in Lawrenceville, Ga. All 40 baits were consumed either immediately or within an hour of placement.

EXAMPLE 5

Free-roaming street dogs in two rural towns in the state of Puebla, Mexico were offered the baits of Example 1 during a field test in January 1990. When the bait was thrown to the 87 individual street dogs, 77% were completely consumed. Only one bait was partially consumed and 22% were rejected, primarily because some stray dogs became frightened and fled when baits were thrown in their direction. However, when fleeing dogs were excluded from the tabulation, bait consumption approached 90% to 95%.

Testing was conducted using captive raccoons to determine response to seven different bait matrices. Tallow and/or beeswax was used in several of the test baits either as binders or to elevate the melting temperatures of the primary matrix material. The seven bait matrices tested were (1) a mixture of Hershey's milk chocolate (80%) and beeswax (20%), (2) peanut butter (80%) and beeswax (20%), (3) sardines in olive oil (80%) and beeswax (20%), (4) canned fish cat food (50%) with tallow and beeswax mixture (50%), (5) a 5.0 cm length of commercially sold fruit bar (Sunkist strawberry N'Grape Two-T-Fruit), (6) a corn meal bait (approximately 2.0 ×5.0 cm) made of corn meal and water batter deep fired in corn oil, and (7) a melted tallow (80%) and beeswax (20%) mixture to which had been added methyl anthranilate (MA), a food flavoring (grape) that is aversive to birds. One percent of a mixture containing 35% MA and 65% starch was added to the tallow-Beeswax to make the test bait. The MA treated bait was of particular interest because crows are a major non-target scavenger of baits intended for raccoon and red fox. A grape-flavored bait readily accepted by raccoons but avoided by crows would be particularly desirable.

In the past, baits aimed at targeting carnivores often were coated with substances such as sugar, blood, and fish or liver meals. To test suitable coatings baits using beef tallow (about 80%) and yellow beeswax (about 20%) were coated with various meals or powders to determine which, if any, were preferred over the tallow/beeswax baits without coatings. Nine different coatings were applied to baits by shaking the baits in a plastic bag containing the candidate material. Depending on their physical properties, the amount of test material that adhered to the baits varied from 2% to 6% of total bait weight. The nine coatings used and tested on captive raccoons included dried or freeze-dried powders which adhered sufficiently to provide adhering coatings that varied from 2% to 6% of the bait weight. These included cheese whey (3%), cheddar cheese (3%), buttermilk (3%), apple (2%), banana (6%), methyl anthranilate (3% of MA-starch mixture described above), corn meal (4%), fish meal (2%), and powdered egg (6%). Studies were then done to determine acceptability of the baits to the raccoon population. Baits wherein the matrix was tallow/beeswax construction without the polyurethane sleeve were used for this test. The baits could not be easily molded to hold a vaccine container. The baits were then made using the polyurethane sleeves as described in Example 1. The buttermilk, apple powder and egg powder were all preferred coatings for baits.

EXAMPLE 6

Ten animals were used in a vaccination trial. 2.0 ml capacity paraffin wax ampules and polyurethane sleeves coated with corn muffin batter mix were chosen as a bait. A raccoon poxvirus rabies virus-glycoprotein recombinant preparation (RCN-KB3-JE13 developed by Esposito of the U.S. Public Health Service (CDC)) was used as the test vaccine. It consisted of $2\times10^8$ PFU/2 ml of recombinant in phosphate buffered saline (PBS) containing 20% fetal bovine serum. Because ampules were from an experimental lot made to have thicker side walls than usual, capacity varied somewhat and thus the volume of vaccine dispensed in each varied from 1.4 to 1.6 ml (dosage approximately $1.5\times10^7$ PFU). Melted paraffin wax (74° C.) was used to seal the open end of the ampule. A 0.5 cm thick circular closed cell foam plug was placed on top of the vaccine in order to prevent the hot wax from coming into direct contact with the vaccine and thereby causing a loss of potency. After the sleeve bait had been deep fired, the exterior of each ampule was lubricated with corn oil and then inserted into the cavity within the sleeve.

Caged animals were simultaneously presented with two of the baits. One contained a water-filled ampule and the other a vaccine containing ampule. This was done to determine if differential consumption might be indicative of vaccine rejection due to an aversive taste. When the paired baits (vaccine and placebo) were then fed to caged raccoons, nine of ten raccoons ate one or both baits on the first night of exposure. Food was withheld from the 10th animal and 48 hours later it ate the vaccine bait but rolled the placebo under the kennel door making it unavailable for consumption. Eight of ten animals completely consumed the vaccine-containing baits, but two animals consumed only 75% of the polyurethane sleeve. All ampules were apparently consumed. Of the placebo baits, seven were eaten completely, two only partially, and one, as indicated, was moved out of reach. The results indicated that the vaccine preparation had no adverse affect on bait consumption. No wax ampules were found intact in kennels where one or both baits were consumed. The epoxy floors of each kennel were then examined the morning after baits were placed and all bait and ampule remains were removed and identified for later comparison with results of sera titrations for rabies antibody levels.

All 10 test animals were sedated with ketamine hydrochloride and bled 5 days pre-vaccination and 10, 30, and 60 days post vaccination and sera were tested for rabies virus neutralizing antibodies by rapid fluorescent focus inhibition test. Nine of ten raccoons developed high rabies antibody titers. The raccoon who never seroconverted was one of the two that consumed only 75% of the polyurethane sleeve.

EXAMPLE 7

Raccoons were given baits containing polyethylene capsules and wax ampules, it was found that raccoons usually did not consume the plastic container of the capsules, but emptied them by chewing. However, several were only partially emptied and none was swallowed during a six day test period. It was evident that raccoons were able to distinguish between bait material and plastic containers. Conversely, except for small fragments of wax, all wax ampules were completely consumed along with bait material. Raccoons apparently did not distinguish between the bait matrix and the wax ampule.

EXAMPLE 8

Polyurethane foam sleeves were slipped onto 2.5 cm diameter wooden dowels and dipped in a commercial corn dog batter mix (Pillsbury Product No. 6947, Pillsbury, Minneapolis, Minn. 55402, USA) used by fast food restaurants. The batter was formulated using 43% Pillsbury batter, 8% yellow corn meal, 10% whole milk, and 39% whole eggs. Ingredients were mixed with an electric mixer for 5 minutes. The consistency of the mixture can be adjusted if needed by adding a small amount of milk or corn dog mix. After the dipped sleeves had drained a few seconds, they were deep fried in corn oil (190° )C.) for 20 to 30 seconds, removed from the dowels, and frozen until used.

The versatility of the baits of the instant invention is due at least in part to the absorptive capacity of the polymeric since the sleeves can absorb liquids approximately 20 times the sleeve weight. Because of this "carrying capacity" this bait can be modified to contain biomarkers, food preservatives, water proofing substances, and different flavor coating to increase acceptance in target animals. The sleeve baits show an unusual capacity to protect the vaccine ampule from direct exposure to the sun and to shock, preventing vaccine loss by absorbing the vaccine once the ampule is ruptured. The bait components are inexpensive when produced in large numbers. The capacity of the sleeve makes it possible to vary food textures, since a widely differing selection of batters can be used with the sleeves.

Both bait and ampule size may be reduced to accommodate certain species such as coyotes that tend to accept small size baits more readily.

I claim:

1. A bait used for delivery of active agents to animals comprising at least one attractant bound to a synthetic polymeric support which is a foam sleeve, said support having embedded therein an ampule or capsule containing an active agent.

2. A bait of claim 1 wherein support is a polyurethane open cell foam.

3. A bait of claim 1 wherein the active agent is contained in an ampule.

4. A bait of claim 3 wherein the ampule is made of paraffin.

5. A bait of claim 1 wherein the active agent is a vaccine.

6. A bait of claim 5 wherein the active agent is a rabies vaccine.

7. A bait of claim 4 wherein the active agent is a rabies vaccine.

8. A bait of claim 1 wherein the support is a polyurethane foam that has been dipped in batter and deep-fried.

9. A bit of claim 8 wherein the batter contains corn meal.

10. A method of dosing animals by administration of a bait of claim 1.

11. A method of claim 10 wherein the active agent is a vaccine.

12. A method of claim 11 wherein the vaccine is a rabies vaccine.

13. A bait of claim 8 wherein the active agent is a rabies vaccine.

14. A bait of claim 13 wherein the rabies vaccine is in a paraffin wax ampule.

15. A method of claim 11 wherein the vaccine is contained in a paraffin wax ampule and the synthetic polymeric support is a sleeve of polyurethane foam that has an attractant.

16. A method of claim 15 wherein the sleeve has been dipped in a batter and deep-fried.

17. A method of claim 16 wherein the vaccine is a recombinant rabies vaccine.

* * * * *